US00PP09790P

United States Patent [19]

Wells

[11] Patent Number: Plant 9,790

[45] Date of Patent: Feb. 4, 1997

[54] MINIATURE ROSE PLANT NAMED 'WELANGEL'

[75] Inventor: Verlie Whitson Wells, Brighton, Tenn.

[73] Assignee: Nor'East Miniature Roses, Inc., Rowley, Mass.

[21] Appl. No.: 586,959

[22] Filed: Jan. 16, 1996

[51] Int. Cl.[6] ..... A01H 5/00

[52] U.S. Cl. ..... Plt./9

[58] Field of Search ..... Plt./7.1, 9, 22, Plt./26, 27

*Primary Examiner*—Howard J. Locker

[57] ABSTRACT

WELangel is a miniature rose which can be grown quite satisfactorily in a greenhouse or as a hardy, garden perennial. It blooms continually throughout the growing season with buds and flowers of a bright medium pink blend. Blooms are most often borne singly on stems up to 20 inches long but also in small clusters, and of exhibition quality. This plant is ideal as for use as a specimen plant, in a border, and for cut flowers. The plant grows 24 to 30 inches tall and has dark-green, matte foliage. This variety does need winter protection in severe climates.

1 Drawing Sheet

CROSS REFERENCE

This present invention relates to a new and distinct variety of hardy, bush type plant of the miniature rose class, which bears great resemblance to its seed parent, MORnita, U.S. Plant Pat. No. 5,110 a rose of the miniature rose class, created by R. S. Moore in 1981, and first sold and marketed as Anita Charles by Sequoia Nursery. The flower of this new invention has a brighter orange color at its base and a greater fluctuation of color between the base and the tips of the petals than those of the seed parent, MORnita, U.S. Plant Pat. No. 5,110.

BACKGROUND OF THE INVENTION 1. this invention is a rose plant of the miniature rose class which can be grown quite satisfactorily in a greenhouse, as a garden perennial, as a specimen plant or for cut flowers, needing protection through the winter in severe climates.

2. This present invention relates to a new and distinct variety of miniature rose plant *Rosa chinensis* 'minima'), which was created by crossing MORnita, U.S. Plant Pat. No. 5,110 (marketed and sold under the name Anita Charles as seed parent, with an unnamed seedling, as pollen parent. The varietal denomination of this new rose is WELangel.

This new variety is distinguished by:

Buds and flowers of a bright medium pink with a splash of orange at the base of the petals.

Buds and flowers borne in the same manner as those of its seed parent, MORnita Charles, U.S. Plant Pat. No. 5,110, mostly one to a long stem and sometimes small clusters of 2–3, making them ideal for cut flowers.

An upright and nicely rounded plant of dark green matte foliage.

No fragrance.

Asexual production by cuttings of this new variety as performed in Essex County, Mass. and in San Bernardino County, Calif. shows that all distinguishing characteristics of this rose continually come true to form.

SUMMARY OF THE INVENTION

This new variety, has bright medium pink flowers with a splash of orange at the base of the petals, borne mostly singly on stems up to 20 inches long, and also in small clusters. The plant itself grows 24 to 30 inches tall at maturity, forming an upright mound of pink blend flowers, atop dark green, matte foliage.

BRIEF DESCRIPTION OF THE DRAWING

The accompanying color photograph shows specimen of the flowers of this new variety in different stages of development as seen and grown indoors under plastic, in early October in Essex County, Mass.

BOTANICAL DESCRIPTION OF THE PLANT

Following is a detailed description in outline form pertaining specifically to this new and distinct variety of *Rosa chinensis* 'minima' The Royal Horticulture Society Colour Chart except where common terms of color definition are employed.

Type: Miniature rose (*Rosa chinensis* 'minima'); hardy; outdoors; decorative; specimen plant; cut flowers; potted plant; greenhouse.

Seed parent: MORnita, U.S. Plant Pat. No. 5,110 (Anita Charles).

Pollen parent: Unnamed seedling.

Flowers: Borne mostly singly on stems of up to 20 inches long but also in small clusters of up to three.

Quantity of bloom: Abundant.

Bud:

*Size and form.*—ovate, 11/16 of an inch in length and ½ inch diameter near its base, then tapering to a point.

*Sepals.*—lanceolate in shape; occasionally lightly bearded; extending beyond the tip of the bud by nearly the length of the bud again, near 144A in color.

*Color when sepals first divide.*—Near 51A.

*When petals begin to unfurl.*—A blend of near 51A and 51C from the top down into near 39B.

*Peduncle.*—1¼ inches; straight, erect; color near 144C with a slight tint of 184B.

*Sepals.*—Permanent, remaining attached to receptacle; usually rolled back near petiole, occasionally beyond petiole, then curling up near the ends as the bloom goes by.

Bloom:

*Size when fully open.*—Up to 2¼ inches.

*Form.*—High centered, petals rolling loosely outward as soon as flowers start to open; remaining high centered.

*Petalage under normal conditions.*—30 to 36 petals arranged shingle-like, and 3 to 5 petaloids in the center of the flower in a mixture of colors, 55A being predominant and 21C at the base, and may have a light pink streak up the center.

*Fragrance.*—None.

Petals:

*Texture.*—Thick; inside matte, outside satiny.

*Form.*—Broad fan shaped, with petals laid flat.

Color: From plants grown inside, under plastic in Essex County, Mass., in October, 1995:

*When half open.*—Outer petals: inside surface — near 55A, 55B and 55C blend with 55A being the dominant color. Outside surface — near 51C from the top down blending into 39B, and into 24C from the base up. Inner petals: inside surface — near 47D from the top down into near 39B from the base up; outside surface — near 3B.

*Base of petals at attachment.*—13A.

*Color change as bloom ages.*—From hear 51A, to a mixture and blend of 51A and 51B; to 56A with center petals of 62B and 62C, and 39B towards the center of the bloom, to 54A and near 62A blend on outer petals and 55B and 55C blend on the inner petals with 22C towards the center.

*General tonality.*—Newly opened flower — bright medium pink; Three days open — mixture of pinks with some yellow/orange.

*Tonality from a distance.*—Bright medium pink.

Lasting quality:

*On plant.*—6 to 9 days depending on conditions.

*As a cut flower.*—5 to 8days or longer, depending on temperature.

Reproductive organs:

*Stamens.*—An average amount — 60 to 70; arranged regularly around styles.

*Filaments.*—Short, uneven in length, from 1/16 to 1/8 inches; color — yellow/orange, near 33B.

*Anthers.*—IID in color.

*Pollen.*—Small amount; orange/yellow, near 15A in color.

*Pistils.*—Some, less than average.

*Styles.*—Very thin; uneven in length; near 53B in color.

*Stigmas.*—Color — IID.

*Hips.*—None observed to maturity; but to near 1/2 inch in diameter and near 144A in color, seeds protruding, and nearly urn shaped.

Plants:

*Habit.*—Upright, well branched, uniform.

*Growth.*—Vigorous, growing to 24 to 30 inches or more at maturity.

*Foliage.*—Small, compound of five (sometimes three or seven) leaflets. Color: new foliage, upper surface — near 146A, lightly flushed with 184A; under side — near 148B, flushed with 182A. Old foliage, upper surface — near 147A; under side — near 138B.

*Leaflet.*—Shape — ovate with acute tip; texture, upper surface — matte, underside — matte; edge — fine, even serration.

*Rachis.*—Color, upper surface — near 137A, under side — near 146B; a few prickles and hairs along the underside of the leaf stem.

*Stipules.*—Very finely serrated, usually even in length, coming to a point away from the stem; usually about 5/16 of an inch in length but observed up to 11/16 of an inch on a seven leaflet leaf.

*New wood.*—Smooth with a color near 182B.

*Old wood.*—Near 137C in color, with stems becoming more coated with 166A as the plant ages.

*Resistance to diseases.*—Average.

*Thorns.*—On main stalk: few, small in size. On laterals from main stalk; three to four per inch; positioned in an irregular manor; near 181A in color; sometimes angled very slightly downward, sometimes curved slightly downward, occasionally straight out to a fine point.

*Prickles.*—Only on the underside of the leaf stems.

The miniature rose plant and its flowers described herein may vary in color and in other slight detail due to climate, soil and cultural conditions under which the variety may be grown; the present description being of the new variety as grown inside under plastic in Essex County, Mass. in the month of October.

The following is claimed:

1. A new and distinct variety of miniature rose plant of vigorous, hardy, upright, and well branched habit, substantially as illustrated and described, characterized by buds and flowers of a bright medium pink with some yellow/orange at the base of the petals, borne mostly singly on long stems up to 20 inches long for use as cut flowers or for exhibition; also borne in small clusters making it a good specimen plant; and further characterized by a compact plant with ample dark green, matte foliage creating a plant that is attractive as a pot plant or garden perennial, and easy to propagate from cuttings.

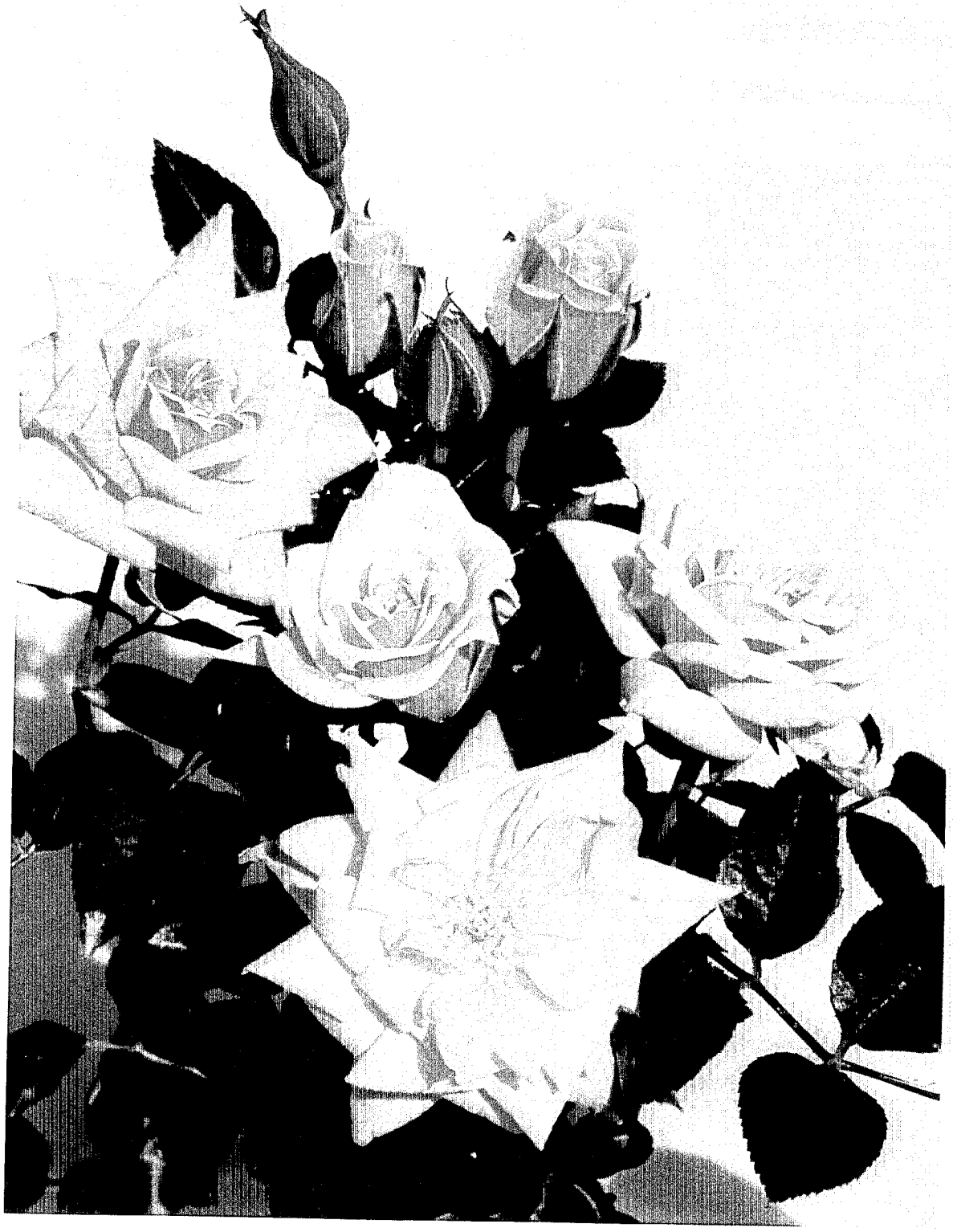

* * * * *